(12) United States Patent
Gysling et al.

(10) Patent No.: US 7,197,942 B2
(45) Date of Patent: *Apr. 3, 2007

(54) APPARATUS FOR MEASURING VELOCITY AND FLOW RATE OF A FLUID HAVING A NON-NEGLIGIBLE AXIAL MACH NUMBER USING AN ARRAY OF SENSORS

(75) Inventors: Daniel L. Gysling, Glastonbury, CT (US); Douglas H. Loose, Southington, CT (US)

(73) Assignee: CiDRA Corporation, Wallington, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/862,237

(22) Filed: Jun. 7, 2004

(65) Prior Publication Data

US 2005/0005712 A1 Jan. 13, 2005

Related U.S. Application Data

(60) Provisional application No. 60/476,460, filed on Jun. 5, 2003, provisional application No. 60/479,744, filed on Jun. 18, 2003.

(51) Int. Cl.
*G01F 1/32* (2006.01)
*G01N 29/02* (2006.01)
(52) U.S. Cl. .................................. 73/861.23; 73/24.01
(58) Field of Classification Search ............. 73/861.23, 73/861.42, 861.44, 861.08; 702/45, 47, 50
See application file for complete search history.

(56) References Cited

U.S. PATENT DOCUMENTS

| 4,048,853 | A | 9/1977 | Smith et al. ............. 73/861.25 |
| 4,080,837 | A | 3/1978 | Alexander et al. ......... 73/61.45 |
| 4,248,085 | A | 2/1981 | Coulthard ................ 73/861.06 |

(Continued)

FOREIGN PATENT DOCUMENTS

| WO | WO 93/14382 | 7/1993 |
| WO | WO 99/067629 | 12/1999 |
| WO | WO 023136 | 3/2002 |

OTHER PUBLICATIONS

"Noise and Vibration Control Engineering Principles and Applications", Leo L. Beranek and Istvan L. Ver, A. Wiley Interscience Publication, pp. 537-541, Aug. 1992.

(Continued)

*Primary Examiner*—Harshad Patel
(74) *Attorney, Agent, or Firm*—Robert D. Crawford, Esq.

(57) ABSTRACT

An apparatus 10 and method is provided that includes a spatial array of unsteady pressure sensors 15–18 placed at predetermined axial locations $x_1$–$x_N$ disposed axially along a pipe 14 for measuring the velocity and volumetric flow rate of a single phase or multi-phase fluid 12 having a non-negligible axial Mach number flowing in the pipe 14. The pressure sensors 15–18 provide acoustic pressure signals $P_1(t)$–$P_N(t)$ to a signal processing unit 30 which determines the speed of sound propagating with and against the flow of the fluid 12 in the pipe 14 using acoustic spatial array signal processing techniques. The apparatus, responsive to the measured speed of sound propagating with and against the flow of the fluid, determines the velocity and the flow rate of the fluid propagating through the pipe.

45 Claims, 5 Drawing Sheets

U.S. PATENT DOCUMENTS

| | | | |
|---|---|---|---|
| 4,445,389 A | 5/1984 | Potzick et al. | 73/861.27 |
| 4,896,540 A | 1/1990 | Shakkottai et al. | 73/861.02 |
| 5,040,415 A | 8/1991 | Barkhoudarian | 73/861.03 |
| 5,083,452 A | 1/1992 | Hope | 73/61 R |
| 5,218,197 A | 6/1993 | Carroll | 250/227.19 |
| 5,285,675 A | 2/1994 | Colgate et al. | 73/23.2 |
| 5,367,911 A | 11/1994 | Jewell et al. | 73/861.08 |
| 5,398,542 A | 3/1995 | Vasbinder | 73/40.5 |
| 5,421,212 A | 6/1995 | Mayranen et al. | 73/861.29 |
| 5,524,475 A | 6/1996 | Kolpak et al. | 73/19.03 |
| 5,526,844 A | 6/1996 | Kamen et al. | 137/614.11 |
| 5,591,922 A | 1/1997 | Segeral et al. | 73/861.04 |
| 5,741,980 A | 4/1998 | Hill et al. | 73/861.04 |
| 5,770,805 A | 6/1998 | Castel | 73/861.04 |
| 5,770,806 A | 6/1998 | Hiismaki | 73/861.29 |
| 5,835,884 A | 11/1998 | Brown | 73/861.04 |
| 5,845,033 A | 12/1998 | Berthold et al. | 385/12 |
| 5,948,959 A | 9/1999 | Peloquin | 73/1.83 |
| 6,016,702 A | 1/2000 | Maron | 73/705 |
| 6,151,958 A | 11/2000 | Letton et al. | 73/61.79 |
| 6,202,494 B1 | 3/2001 | Riebel et al. | 73/861.29 |
| 6,354,147 B1 | 3/2002 | Gysling et al. | 73/61.79 |
| 6,378,357 B1 | 4/2002 | Han et al. | 73/54.41 |
| 6,435,030 B1 | 8/2002 | Gysling et al. | 73/587 |
| 6,463,813 B1 | 10/2002 | Gysling | 73/862.59 |
| 6,536,291 B1 | 3/2003 | Gysling et al. | 73/861.42 |
| 6,550,342 B2 | 4/2003 | Croteau et al. | 73/800 |
| 6,587,798 B2 | 7/2003 | Kersey et al. | 702/50 |
| 6,601,458 B1 | 8/2003 | Gysling et al. | 73/861.04 |
| 6,609,069 B2 | 8/2003 | Gysling | 702/48 |
| 6,691,584 B2 | 2/2004 | Gysling et al. | 73/861.42 |
| 6,732,575 B2 | 5/2004 | Gysling et al. | 73/61.79 |
| 6,782,150 B2 | 8/2004 | Davis et al. | 385/12 |
| 6,813,962 B2 | 11/2004 | Gysling et al. | 73/861.26 |
| 6,837,098 B2 | 1/2005 | Gysling et al. | 73/61.79 |
| 6,874,361 B1 * | 4/2005 | Meltz et al. | 73/152.32 |
| 7,032,432 B2 * | 4/2006 | Gysling et al. | 73/24.01 |
| 2002/0100327 A1 | 8/2002 | Kersey et al. | 73/597 |
| 2002/0123852 A1 | 9/2002 | Gysling et al. | |
| 2002/0129662 A1 | 9/2002 | Gysling et al. | |
| 2003/0038231 A1 | 2/2003 | Bryant et al. | |
| 2003/0136186 A1 | 7/2003 | Gysling et al. | |
| 2003/0154036 A1 | 8/2003 | Gysling et al. | |
| 2004/0016284 A1 | 1/2004 | Gysling et al. | |
| 2004/0069069 A1 | 4/2004 | Croteau | |
| 2004/0074312 A1 | 4/2004 | Gysling | |
| 2004/0144182 A1 | 7/2004 | Gysling et al. | |
| 2004/0168523 A1 | 9/2004 | Bailey et al. | |
| 2004/0199341 A1 | 10/2004 | Gysling et al. | |
| 2004/0210404 A1 | 10/2004 | Gysling et al. | |
| 2004/0226386 A1 | 11/2004 | Croteau et al. | |
| 2004/0231431 A1 | 11/2004 | Bailey et al. | |
| 2004/0255695 A1 | 12/2004 | Gysling et al. | |

OTHER PUBLICATIONS

"Two Decades of Array Signal Processing Research", The Parametric Approach, H. Krim and M. Viberg, IEEE Signal Processing Magazine, Jul. 1996, pp. 67-94.

"Development of an array of pressure sensors with PVDF film, Experiments in Fluids 26", Jan. 8, 1999, Springer-Verlag.

* cited by examiner

APPARATUS FOR MEASURING VELOCITY AND FLOW RATE OF A FLUID HAVING A NON-NEGLIGIBLE AXIAL MACH NUMBER USING AN ARRAY OF SENSORS

CROSS-REFERENCE TO RELATED PATENT APPLICATIONS

This application claims the benefit of U.S. Provisional Patent Application Ser. No. 60/476,460 filed Jun. 5, 2003, and U.S. Provisional Patent Application Ser. No. 60/479,744 filed Jun. 18, 2003, both of which are incorporated by reference herein in their entirety.

TECHNICAL FIELD

This invention relates to an apparatus for measuring parameters of a fluid passing within a pipe, and more particularly to an apparatus for measuring velocity and flow rate of a fluid having a non-negligible axial Mach number using an array of sensors.

BACKGROUND

An industrial fluid system typically includes the flow of fluid through tubes, pipes, ducts, or other conduits (hereinafter, "pipes") as well as through fluid control devices such as pumps, valves, orifices, heat exchangers, and the like. Fluid systems are found in many different industries such as the oil and gas industry, refining, food and beverage industry, chemical and petrochemical industry, pulp and paper industry, power generation, pharmaceutical industry, and water and wastewater treatment. The fluid within the fluid system may be a single phase fluid (e.g., gas, liquid or liquid/liquid mixture) and/or a multi-phase mixture (e.g. paper and pulp slurries or other solid/liquid mixtures). The multi-phase mixture may be a two-phase liquid/gas mixture, a solid/gas mixture or a solid/liquid mixture, gas entrained liquid or a three-phase mixture.

Operation of a fluid system often requires that various parameters of the fluid be monitored. The parameters may be used as feedback for quality control or may be used to detect problems or needed maintenance in the system. These parameters may include velocity and volumetric flow rate of the fluid, among others.

The ability to measure velocity and flow rate of a fluid within a pipe is an important aspect of any system or strategy design to optimize the performance of a fluid system, particularly in a fluid system based on saturated vapor/liquid mixtures. The industry recognizes this, and has been developing a wide variety of technologies to perform this measurement. These include probe based devices, sampling devices, venturis and ultrasonic devices. While these technologies may be effective, they are not without their drawbacks. For example, typical meters are invasive. That is, they are installed such that they are in contact with the fluid in the fluid system. As a result, installation or maintenance of the meter often requires at least a portion of the fluid system to be isolated.

SUMMARY OF THE INVENTION

Objects of the present invention include providing a system for measuring the speed of sound propagating through a fluid flowing in pipes in industrial processes and other related processes, for example, having a non-negligible axial Mach number to determine the volumetric flow rate of the fluid.

In one aspect of the present invention, an apparatus for measuring at least one parameter of a fluid having a non-negligible axial Mach number passing through a pipe is provided. A spatial array includes at least two pressure sensors, disposed at different axial locations along the pipe. Each of the pressure sensors measures an unsteady pressure within the pipe at a corresponding axial location. Each of the sensors also provides a pressure signal in response to a first one-dimensional acoustic wave propagating in a first axial direction and a second one-dimensional acoustic wave propagating in a second axial direction within the pipe, the first axial direction being opposite the second axial direction. A signal processor, which is responsive to the pressure signals, provides a first acoustic signal indicative of the speed of sound of the first acoustic wave and a second acoustic signal indicative of the second acoustic wave.

In one embodiment, an apparatus measures at least one parameter of a fluid having a non-negligible axial Mach number passing through a pipe. The apparatus comprises a spatial array of at least two pressure sensors and a signal processor. The pressure sensors are disposed at different axial locations along the pipe, and each measures an unsteady pressure within the pipe at a corresponding axial location. Each of the pressure sensors provides a pressure signal in response to a first one-dimensional acoustic wave propagating in a first axial direction and a second one-dimensional acoustic wave propagating in a second axial direction within the pipe, the first axial direction being opposite the second axial direction. The signal processor provides a velocity signal indicative of the velocity of the fluid in response to a difference between a speed of the first acoustic wave and a speed of the second acoustic wave. The signal processor may determine the volumetric flow rate of the fluid using the velocity signal. The signal processor may also determine a speed at which sound propagates through the fluid using a ratio of the speed of the first acoustic wave and the speed of the second acoustic wave.

In another aspect of the present invention, a method for measuring at least one parameter of a fluid having a non-negligible axial Mach number passing through a pipe is provided. The method includes measuring unsteady pressures within the pipe at at least two predetermined axial measurement locations along the pipe to provide a pressure signal in response to a first one-dimensional acoustic wave propagating in a first axial direction and a second one-dimensional acoustic wave propagating in a second axial direction within the pipe, the first axial direction being opposite the second axial direction. The method then determines a first acoustic signal indicative of the speed of sound of the first acoustic wave; and a second acoustic signal indicative of the second acoustic wave.

In one embodiment, a method for measuring the volumetric flow rate of a fluid having a non-negligible axial Mach number passing through a pipe comprises: measuring unsteady pressures within the pipe at at least two predetermined axial measurement locations along the pipe to provide a pressure signal in response to a first one-dimensional acoustic wave propagating in a first axial direction and a second one-dimensional acoustic wave propagating in a second axial direction within the pipe, the first axial direction being opposite the second axial direction; and determining a velocity of the fluid in response to a difference between a speed of the first acoustic wave and a speed of the second acoustic wave. The method may further comprise determining a flow rate of the fluid in response to the velocity of the fluid, and may further comprise determining a speed at which sound propagates through the fluid using a ratio of the speed of the first acoustic wave and the speed of the second acoustic wave.

The foregoing and other objects, features and advantages of the present invention will become more apparent in light of the following detailed description of exemplary embodiments thereof.

DETAILED DESCRIPTION

Figure 1:
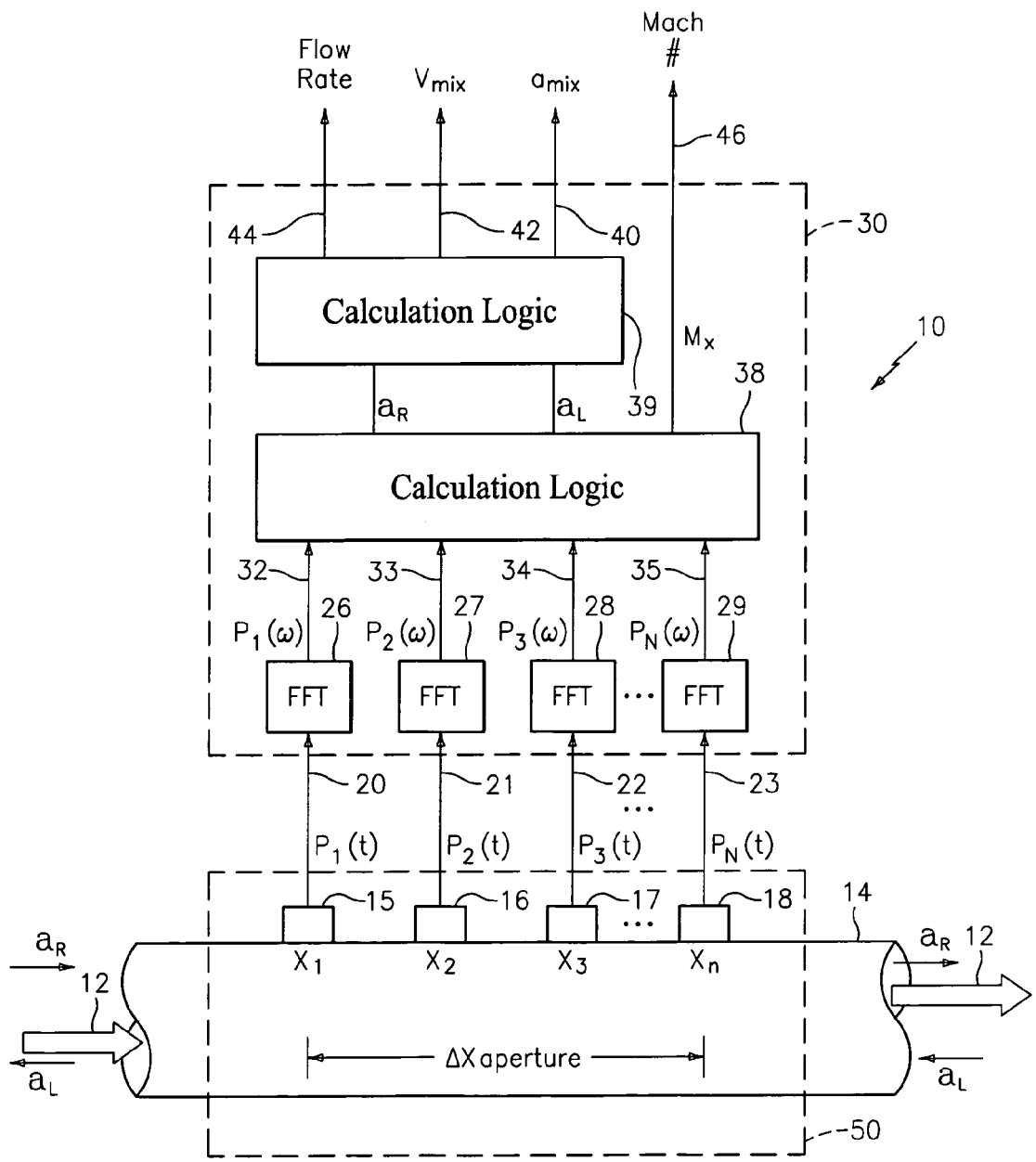
FIG. 1 is a block diagram of a flow meter for measuring the speed of sound propagating with and against the direction of flow of a fluid within a pipe, in accordance with the present invention.

Systems that utilize, emit or process single phase and multi-phase fluids (or mixtures) having non-negligible axial Mach numbers, such as liquid, gas, liquid/gas, liquid/solid, solid/gas, etc., are found in many industrial processes. Referring to FIG. 1, the present invention provides an apparatus 10 for measuring the velocity and flow rate of such a fluid 12 passing through a pipe 14 by measuring the speed of propagation of an acoustic wave of the fluid in the direction of the fluid flow ($\alpha_R$) and the speed of propagation of an acoustic wave through the fluid against the direction of the fluid flow ($\alpha_R$) using an array of pressure sensors 15, 16, 17, and 18. As used herein, the term "fluid" includes any single phase fluid or multi-phase fluid or mixture. Also, as used herein, the term "pipe" includes any conduit for the flow of fluid. The measurement of the volumetric flow rate of the fluid is therefore based on the differential speed of sound. The accuracy of the velocity and volumetric flow rate measurements scales with the inverse of the axial Mach number (Ma). As will be appreciated, the present invention is well suited for velocity and volumetric flow rate measurements of gas and steam.

Acoustic waves are known to propagate through the fluid contained in a pipe. If the temporal frequency of an acoustic wave is below a so called cut-on frequency, propagation of the acoustic wave through the pipe will occur along the longitudinal axis of the pipe only as one-dimensional pressure waves. That is, there will be no radial variation to the acoustic pressure. For circular pipes, this cut-on frequency is given as a function of the speed of sound of the fluid at rest (SOS) and pipe inside diameter (D):

$$f_{cut-on} = \frac{1.84}{\pi D} SOS \quad (1)$$

For example, a 6-inch ANSI schedule 40 pipe filled with air near ambient conditions has a cut-on frequency of approximately 1400 Hz. For a similar pipe containing water, the cut-on frequency is approximately 6000 Hz. The cut-on frequency for air in an 8-inch pipe for example is around 1000 Hz, meaning that any acoustic wave below 1000 Hz will propagate through the fluid in the pipe only as a one-dimensional plane wave.

The propagation speed of a one-dimensional acoustic wave will appear to travel faster or slower relative to a stationary observer (i.e. the pipe wall) depending on whether the acoustic wave propagation direction is in the same direction of the bulk flow or in the opposite direction of the bulk flow, respectively. The amount of increase or decrease of the apparent acoustic propagation speed or velocity is equal or nearly equal to the velocity of the bulk flow. If the fluid in the pipe is not flowing, the propagation speed of the acoustic wave will appear the same in both directions.

The present invention takes advantage of these two properties of acoustic field inside a pipe to measure the fluid velocity and, in turn, the volumetric flow rate of the fluid in the pipe. Knowing that acoustic waves below the cut-on frequency will propagate only in the longitudinal direction of the pipe at the speed of sound plus (or minus) the flow velocity when propagating in the same (or opposite) direction of the flow, the volumetric flow rate of the fluid can be determined by separately measuring the speed of propagation in the direction of the bulk flow and in the direction opposite the bulk flow and using the difference of the two measurements to determine the flow velocity. In addition, the speed of sound of the fluid, and thus certain fluid properties, can be determined by averaging the two measurements, as will be described in greater detail hereinafter.

The axial Mach number (Mx) is a non-dimensional number defined as the ratio of the mean fluid flow velocity ($V_{mix}$) over the speed of sound of the fluid at rest (SOS):

$$Mx = V_{mix}/SOS \quad (2)$$

The measurement method of the present invention is practical for Mach numbers greater than zero (non-negligible) since the uncertainty in the bulk flow velocity measurement is proportional to 1/Mx. In most gas/vapor flows Mx>0.02, which is sufficient to measure the flow rate with good certainty, and in fact Mx is typically between 0.1 and 0.2.

The acoustic propagation speeds $\alpha_R$ and $\alpha_L$ are determined using the array of sensors 15–18, which are attached to the pipe (preferably, but not required to be, a non-intrusive and/or clamp-on design) and array processing algorithms, as will be described in greater detail hereinafter. One feature of the array processing algorithm of the present invention is that the speed of propagation is measured independently in both longitudinal directions of the pipe. The flow velocity is then equal to one-half the difference of the two results ($\alpha_R$ and $\alpha_L$), as will be described in greater detail hereinafter.

This method of measuring the flow velocity and volumetric flow rate is not dependent on the source of the acoustic wave, and the frequencies of interest are generally below 2 kHz. The only requirement is that there are waves propagating in both directions through the sensor array. In any industrial application, acoustic waves propagating through the pipe will naturally occur at the frequency range of interest due to various sound sources, i.e. pumps, compressors, turbines, expanders, valves, orifice plates, the flow itself, etc. In contrast, other existing methods such as ultrasonic, for example, require a separate source to generate sound at ultrasonic frequencies in the 1 MHz range.

The present method of determining the volumetric flow rate of the fluid 12 within pipe 14 relies on the interaction of the bulk fluid flow with the acoustic pressure field. The interaction results in sound waves propagating with the bulk flow traveling at the speed of sound of the fluid 12 (SOS) plus the mean fluid flow velocity (Vmix) and, conversely, sound waves traveling against the bulk flow propagating at the SOS minus Vmix. That is, $$\alpha_R = SOS + V_{mix} \quad (3)$$

$$\alpha_L = SOS - V_{mix} \quad (4)$$

where $\alpha_R$=velocity of a right traveling acoustic wave relative to a stationary observer (i.e. the pipe 14), and $\alpha_L$=velocity of a left traveling acoustic wave apparent to a stationary observer. Combining these two equations yields an equation for the mean velocity:

$$V_{mix} = (\alpha_R - \alpha_L)/2 \quad (5)$$

Combining these two equations also yields an equation for the speed of sound of the fluid:

$$SOS = (\alpha_R + \alpha_L)/2 \quad (6)$$

Therefore, by measuring the propagation velocity of acoustic waves in both directions relative to the stationary pipe ($\alpha_R$ and $\alpha_L$), the mean flow velocity can be determined. The volumetric flow through the pipe may then be calculated by multiplying the mean flow velocity by the cross-sectional area of the pipe 14. In addition, by measuring $\alpha_R$ and $\alpha_L$, the speed of sound of the fluid can be determined. Using the speed of sound of the fluid, certain properties of the fluid (e.g., percent composition) can be determined.

The practicality of using this method to determine the mean fluid flow velocity is predicated on the ability to resolve the sound speed in both directions with sufficient accuracy to determine the volumetric flow. The relative uncertainty in mixture flow velocity is proportional to the relative uncertainty in sound speed divided by the axial Mach number. Thus, the method becomes unfeasible as the axial Mach number approaches zero. For most liquid based flow applications, the axial Mach numbers are quite small. The speed of sound in most liquids is upwards of 4000 ft/sec and mixture flow velocities tend to be limited to ~10 ft/sec, resulting in axial Mach numbers on the order of ~0.0025. For a +/−10% accuracy in flow rate (+/−1 ft/sec), the sound speed of the upstream and downstream propagating waves would need to be resolved to +/−0.5/4000 or 1 part in 8,000. This is not the case, however, for many gas and steam applications where flow velocity are higher and sound speeds lower, resulting flows that often have axial Mach numbers of 0.1 or greater. For saturated vapor/liquid flows, to resolve the flow rate to 10% accuracy (or +/−7 ft/sec), one would have to resolve the sound speed to +/−3.5 ft/sec, or 3.5/700 or 1 part in 200.

Referring to FIG. 1, the apparatus 10 for measuring the velocity and volumetric flow rate of a single or multi-phase fluid 12 passing through a pipe 14 is shown. As discussed above, the apparatus 10 measures the velocity and flow rate of the fluid 12 passing through pipe 14 by measuring the speed of propagation of an acoustic wave through the fluid 12 in the direction of the fluid flow ($\alpha_R$) and the speed of propagation of an acoustic wave through the fluid 12 against the direction of the fluid flow ($\alpha_L$) using an array of pressure sensors 15–18. The measurement of the velocity of the fluid 12 is therefore based on the differential speed of sound, and the measurement of the volumetric flow rate of the fluid 12 is, in turn, based on the measured velocity. As one example, the apparatus 10 will be discussed in the context of a steam delivery system, but one will appreciate that the apparatus 10 can be applied to any number of other applications.

As described hereinbefore, the apparatus 10 is configured and programmed to measure and process the detected unsteady pressures $P_1(t)$–$P_N(t)$ created by one-dimensional acoustic waves propagating through the fluid 12 to determine parameters of the fluid 12. As shown in FIG. 1, the flow meter 10 has an array of at least two acoustic pressure sensors (e.g., 15, 16) located at two locations $x_1$, $x_2$ axially along the pipe 14. One will appreciate that the sensor array may include more than two pressure sensors as depicted by pressure sensors 17 and 18 at locations $x_3$, $x_N$.

The pressure generated by the one-dimensional acoustic waves may be measured through holes in the pipe 14 ported to external pressure sensors 15–18 or by other techniques discussed hereinafter. The pressure sensors 15–18 provide pressure time-varying signals $P_1(t), P_2(t), P_3(t), P_N(t)$ on lines 20,21,22,23 to a signal processing unit 30 to known Fast Fourier Transform (FFT) logics 26,27,28,29, respectively. The FFT logics 26–29 calculate the Fourier transform of the time-based input signals $P_1(t)$–$P_N(t)$ and provide complex frequency domain (or frequency based) signals $P_1(\omega), P_2(\omega), P_3(\omega), P_N(\omega)$ on lines 32,33,34,35 indicative of the frequency content of the input signals. Instead of FFT's, any other technique for obtaining the frequency domain characteristics of the signals $P_1(t)$–$P_N(t)$, may be used. For example, the cross-spectral density and the power spectral density may be used to form a frequency domain transfer functions (or frequency response or ratios) discussed hereinafter.

The frequency signals $P_1(\omega)$–$P_N(\omega)$ are fed to Calculation Logic 38, which provides a signal to line 40 indicative of the speed of sound of the fluid 12, $a_{mix}$ (where $a_{mix}$=SOS), a signal to line 42 indicative of the mean velocity of the fluid 12, $V_{mix}$, and a signal to line 44 indicative of the volumetric flow rate of the fluid 12. If the Mach number Mx is not negligible and is desired, the calculation logic 38 may also provide a signal Mx to line 46 indicative of the Mach number Mx.

More specifically, for planar one-dimensional acoustic waves in a homogenous mixture, it is known that the acoustic pressure field P(x,t) at a location x along pipe 14, where the wavelength λ of the acoustic waves to be measured is long compared to the diameter d of the pipe 14 (i.e., λ/d>>1), may be expressed as a superposition of a right traveling wave and a left traveling wave, as follows:

$$P(x,t) = (Ae^{-ik_r x} + Be^{+ik_l x})e^{i\omega t} \quad (7)$$

where A,B are the frequency-based complex amplitudes of the right and left traveling waves, respectively, x is the pressure measurement location along the pipe 14, ω is frequency (in rad/sec, where ω=2πf), and $k_r, k_l$ are wave numbers for the right and left traveling waves, respectively, which are defined as:

$$k_r \equiv \left(\frac{\omega}{a_{mix}}\right)\frac{1}{1+M_x} \quad \text{and} \quad k_l \equiv \left(\frac{\omega}{a_{mix}}\right)\frac{1}{1-M_x} \quad (8)$$

where amix is the speed of sound of the fluid 12 (mixture) in the pipe 14, ω is frequency (in rad/sec), and $M_x$ is the axial Mach number of the flow of the fluid 12 within the pipe 14:

$$M_x \equiv \frac{V_{mix}}{a_{mix}} \qquad (9)$$

where $V_{mix}$ is the velocity of the fluid 12. For non-homogenous mixtures, the axial Mach number represents the average velocity of the fluid 12 and the low frequency acoustic field description remains substantially unaltered.

The data from the array of sensors 15–18 may be processed in any domain, including the frequency/spatial domain, the temporal/spatial domain, the temporal/wavenumber domain or the wave-number/frequency (k-ω) domain. As such, any known array processing technique in any of these or other related domains may be used if desired, similar to the techniques used in the fields of SONAR and RADAR.

Figure 2:
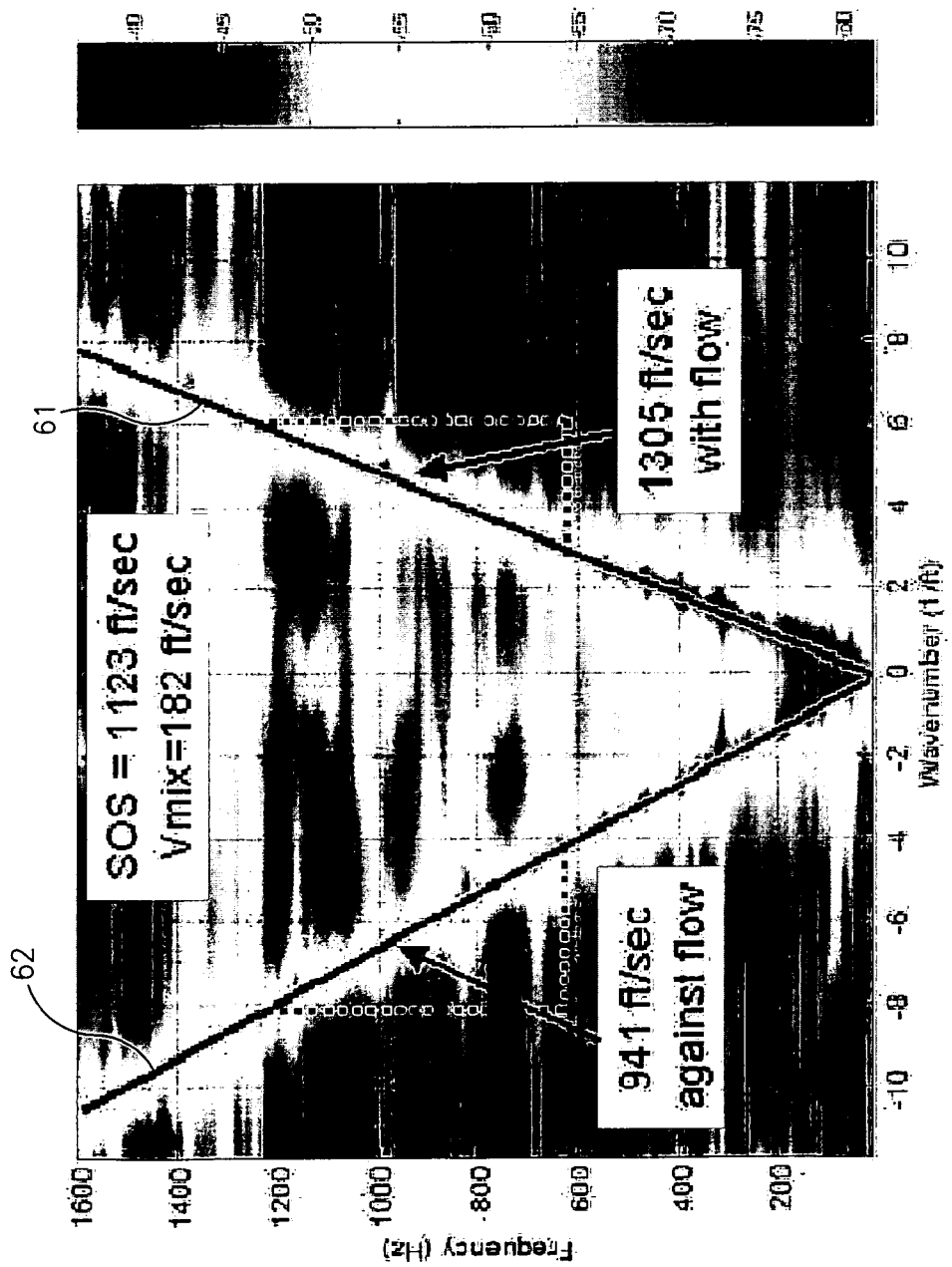
FIG. 2 is a kω plot of data processed from an array of pressure sensors use to measure the speed of sound propagating through a gas flowing in a pipe, in accordance with the present invention.

One such technique of determining the speed of sound propagating through the fluid 12 is using array processing techniques to define acoustic ridges 61 and 62 in the k-ω plane as shown in FIG. 2. This technique is similar to that described in U.S. Pat. No. 6,587,798 filed Nov. 28, 2001, titled "Method and System for Determining The Speed of Sound in a Fluid Within a Conduit", which is incorporated herein by reference.

In response to receiving the time-based pressure signals $P_1(t)$–$P_N(t)$ from the pressure sensors 15–18, the signal processor 24 performs a Fast Fourier Transform (FFT) of the time-based pressure signals $P_1(t)$–$P_N(t)$ to convert the pressure signals into the frequency domain. The power of the frequency-domain pressure signals are then determined and defined in the k-ω plane by using array processing algorithms (such as Capon and Music algorithms). The acoustic ridges in the k-ω plane, as shown in the k-ω plot of FIG. 2, are then determined.

The device 10 of the present invention uses known array processing techniques, in particular the Minimum Variance, Distortionless Response (MVDR, or Capon technique), to identify pressure fluctuations, which convect with the materials flowing in a conduit and accurately ascertain the velocity, and thus the flow rate, of said material. These processing techniques utilize the covariance between multiple sensors 15–18 at a plurality of frequencies to identify signals that behave according to a given assumed model.

To calculate the power in the k-ω plane, as represented by a k-ω plot (see FIG. 2) of the pressure signals, the processor 58 determines the wavelength and so the (spatial) wavenumber k, and also the (temporal) frequency and so the angular frequency ω, of various spectral components of the acoustic waves created passively or actively within the pipe 14. There are numerous algorithms available in the public domain to perform the spatial/temporal decomposition of arrays of sensor units 15–18.

In the case of suitable acoustic pressures being present, the power in the k-ω plane shown in the k-ω plot of FIG. 2 so determined will exhibit structures that are called acoustic ridges, as indicated at 61 and 62. Such a plot will indicate a tendency for k-ω pairs to appear more or less along a line with some slope, the slope indicating the speed of sound traveling in both directions, as is described in more detail below. The power in the k-ω plane so determined is then provided to an acoustic ridge identifier in processor 30, which uses one or another feature extraction method to determine the location and orientation (slope) of any acoustic ridge present in the k-ω plane.

Because sound propagates in both directions through the pipe 14, the acoustic power is located along two acoustic ridges, a first ridge (61) for the sound traveling with the flow at a speed of $a_{mix}+V_{mix}$, and a second ridge (62) for the sound traveling against the flow at a speed of $a_{mix}-V_{mix}$. In the example provided herein, the slope of the first acoustic ridge 61 is equal to the velocity $\alpha_R$ of the right traveling acoustic wave, and the slope of the second acoustic ridge 62 is equal to the velocity $\alpha_L$ of the left traveling acoustic wave. The dashed lines show the best-fit two-variable maximization of the power with the two variables being sound speed and flow velocity. In FIG. 2, the right-side ridge 61 represents the acoustic wave traveling in the same direction as the fluid 12 flow and therefore its slope is steeper than the left-side ridge 62 that represents the acoustic wave traveling in the opposite direction of the fluid 12 flow. This indicates that the acoustic wave traveling in the same direction of the fluid 12 flow is traveling faster than the acoustic wave traveling in the opposite direction of the fluid 12 flow relative to the stationary pressure sensors 15–18.

The calculation logic 39 determines the velocities $\alpha_L$ and $\alpha_R$ by determining the slope of the acoustic ridges 61 and 62. Using these velocities, the calculation logic 39 then calculates the mean velocity of the fluid 12:

$$V_{mix}=(\alpha_R-\alpha_L)/2 \qquad (10)$$

The calculation logic 39 can then calculate the volumetric flow rate of the fluid 12 by multiplying the mean flow velocity $V_{mix}$ by the cross-sectional area of the pipe 14.

In addition to calculating velocity and volumetric flow of the fluid 12, calculation logic 39 may also calculate the speed of sound (SOS) of the fluid 12:

$$SOS=(\alpha_R+\alpha_L)/2 \qquad (11)$$

As described in U.S. patent application No. 10/766,440 filed Jan. 27, 2004, which is incorporated herein by reference, the speed of sound of the fluid 12 may be used to determine various properties of the fluid 12 such as, for example, gas volume fraction of the fluid 12.

The array processing unit 23 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by k=2π/λ where λ is the wavelength of a spectral component, and corresponding angular frequencies given by ω=2πν.

The prior art teaches many algorithms of use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm.

Also, some or all of the functions within the signal processor 30 may be implemented in software (using a microprocessor or computer) and/or firmware, or may be implemented using analog and/or digital hardware, having sufficient memory, interfaces, and capacity to perform the functions described herein.

Acoustic pressure sensors 15–18 sense acoustic pressure signals that, as measured, are lower frequency (and longer wavelength) signals than those used for ultrasonic flow meters of the prior art, and thus the current invention is more tolerant to inhomogeneities in the flow, such as time and space domain inhomogeneities within the flow.

In addition, the present invention may incorporate the compliance of the pipe 14 to determine the effective speed of sound of a vapor/liquid mixture (fluid) 12 flowing through the pipe 14. The acoustic pressure signals $P_1(t)$–$P_N(t)$ are generated within the vapor/liquid mixture of the pipe 14 by a variety of non-discrete sources such as remote Machinery, mills, pumps, valves, elbows, as well as the vapor/liquid mixture flow itself. It is this last source, the vapor/liquid mixture 12 flowing within the pipe 14, which is a generic source of acoustic noise that assures a minimum level of acoustics for any vapor/liquid mixture piping systems for which the present invention takes unique advantage. The flow generated acoustics increase with mean flow velocity and the overall noise levels (acoustic pressure levels) are a function of the generating mechanism and the damping mechanism. As such, no external discrete noise source is required within the present invention and thus may operate using passive listening. While the flow meter 10 passively listens to the mixture flow 12, the present invention contemplates adding an acoustic source to inject a desired acoustic wave into the fluid 12 to be measured, such as by compressing, vibrating and/or tapping the pipe 14, to name a few examples.

For certain types of pressure sensors 15–18, e.g., pipe strain sensors, accelerometers, velocity sensors or displacement sensors, discussed hereinafter, it may be desirable for the pipe 14 to exhibit a certain amount of pipe compliance.

Alternatively, to minimize any error effects (and the need for the corresponding calibration) caused by pipe compliance, the axial test section 50 of the pipe 14 along where the sensors 15–18 are located may be made as rigid as possible. To achieve the desired rigidity, the thickness of the wall of the test section 50 may be made to have a predetermined thickness, or the test section 50 may be made of a very rigid material, e.g., steel, titanium, Kevlar®, ceramic, or other material with a high modulus. Kevlar is a registered trademark of Dupont, Wilmington, Del.

It is within the scope of the present that the pressure sensor spacing may be known or arbitrary and that as few as two sensors are required if certain information is known about the acoustic properties of the fluid piping system. The pressure sensors 15–18 are spaced sufficiently such that the entire length of the array (aperture) is at least a significant fraction of the measured wavelength of the acoustic waves being measured. As will be described in greater detail, the acoustic wavelength to be measured is a function of at least the size and mass of the droplets, and the viscosity of the vapor. The greater the size and mass of the droplets and/or the less viscous the vapor, the greater the spacing of the sensors is needed. Conversely, the smaller the size and mass of the droplets and/or the more viscous the vapor, the shorter the spacing of the sensors is needed.

For relatively well-mixed vapor/liquid mixtures in which the liquid phase exists as small droplets within a continuous gas phase, the flow can be termed mist flow. Assuming that the droplets of the vapor/liquid mixture are small enough and the acoustic frequencies and the frequencies of perturbations associated with the acoustics are low enough for the droplets of liquid to exhibit negligible slip (both steady and unsteady), the sound speed can be assumed to be substantially non-dispersive (that is constant with frequency) and the volumetric phase fraction of the mixture could be determined through the Wood equation:

$$\rho_{mix} = \sum_{i=1}^{N} \phi_i \rho_i \tag{12}$$

$$\frac{1}{\rho_{mix} a_{mix}^2} = \sum_{i=1}^{N} \frac{\phi_i}{\rho_i a_i^2} \tag{13}$$

$$\sum_{i=1}^{N} \phi_i = 1 \tag{14}$$

For one-dimensional waves propagating within a vacuum backed pipe (or a pipe immersed in large volume of low impedance fluid such as air at atmospheric conditions), the compliance introduced by the pipe (in this case a circular pipe of modulus E, radius R and wall thickness t) reduces the measured sound speed from the infinite dimensional sound speed. The effect of the pipe is given by the following relationship:

$$\frac{1}{\rho_{mix} c_{measured}^2} = \frac{1}{\rho_{mix} c_{mix}^2} + \sigma \text{ where } \sigma \equiv \frac{2R}{Et} \tag{15}$$

The frequency of the speed of sound that is detected for a particular mixture sets the wavelength of interest. The wavelength is the inverse of the frequency, and therefore, the higher the frequency, the shorter the wavelength and vice versa. The wavelength, therefore, defines the aperture ($\Delta x_{aperture}$) of the array (See FIG. 1). As described hereinbefore, the aperture should be at least a significant fraction of the length of the wavelength of the speed of sound of interest. For example, a vapor/liquid mixture having droplets of approximately 30 um has a central frequency ($f_{1/2}$) of approximately 30 Hz, which corresponds to an aperture of approximately 20 ft. Similarly, a vapor/liquid mixture having droplets of approximately 3 um has a central frequency ($f_{1/2}$) of approximately 3 KHz, which corresponds to an aperture of approximately 1 ft. Consequently, the size of the liquid droplet defines the length of the aperture of the flow meter. In other words, the larger the size of the droplet, the longer the aperture needed to measure the speed of sound to determine specific parameters of the mixture. Similarly, the smaller the size of the droplet, the shorter the aperture needed to measure the speed of sound to determine specific parameters of the mixture.

The pressure sensors 15–18 described herein may be any type of pressure sensor, capable of measuring the unsteady (or ac or dynamic) pressures within a pipe 14, such as piezoelectric, optical, capacitive, resistive (e.g., Wheatstone bridge), accelerometers (or geophones), velocity measuring devices, displacement measuring devices, etc. If optical pressure sensors are used, the sensors 15–18 may be Bragg grating based pressure sensors, such as that described in U.S. patent application, Ser. No. 08/925,598, entitled "High Sensitivity Fiber Optic Pressure Sensor For Use In Harsh Environments", filed Sep. 8, 1997, now U.S. Pat. No. 6,016,702, and in U.S. patent application, Ser. No. 10/224,821, entitled "Non-Intrusive Fiber Optic Pressure Sensor for Measuring Unsteady Pressures within a Pipe", which are incorporated herein by reference. Alternatively, the sensors 15–18 may be electrical or optical strain gages attached to or embedded in the outer or inner wall of the pipe which measure pipe wall strain, including microphones, hydrophones, or any other sensor capable of measuring the unsteady pressures within the pipe 14. In an embodiment of the present invention that utilizes fiber optics as the pressure sensors 15–18, they may be connected individually or may be multiplexed along one or more optical fibers using wavelength division multiplexing (WDM), time division multiplexing (TDM), or any other optical multiplexing techniques.

For any of the embodiments described herein, the pressure sensors 15–18, including electrical strain gages, optical fibers and/or gratings among others as described herein, may be attached to the pipe by adhesive, glue, epoxy, tape or other suitable attachment means to ensure suitable contact between the sensor and the pipe 14. The sensors may alternatively be removable or permanently attached via known mechanical techniques such as mechanical fastener, spring loaded, clamped, clam shell arrangement, strapping or other equivalents. Alternatively, the strain gages, including optical fibers and/or gratings, may be embedded in a composite pipe 14. If desired, for certain applications, the gratings may be detached from (or strain or acoustically isolated from) the pipe 14 if desired.

It is also within the scope of the present invention that any other strain sensing technique may be used to measure the variations in strain in the pipe 14, such as highly sensitive piezoelectric, electronic or electric, strain gages attached to or embedded in the pipe 14.

In certain embodiments of the present invention, a piezoelectronic pressure transducer may be used as one or more of the pressure sensors 15–18 and it may measure the unsteady (or dynamic or ac) pressure variations inside the pipe 14 by measuring the pressure levels inside of the pipe. In an embodiment of the present invention, the sensors 14 comprise-pressure sensors manufactured by PCB Piezotronics of Depew, N.Y. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The pressure sensors 15–18 may incorporate a built-in MOSFET microelectronic amplifier to convert the high-impedance charge output into a low-impedance voltage signal. The sensors 15–18 may be is powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

Figure 3:
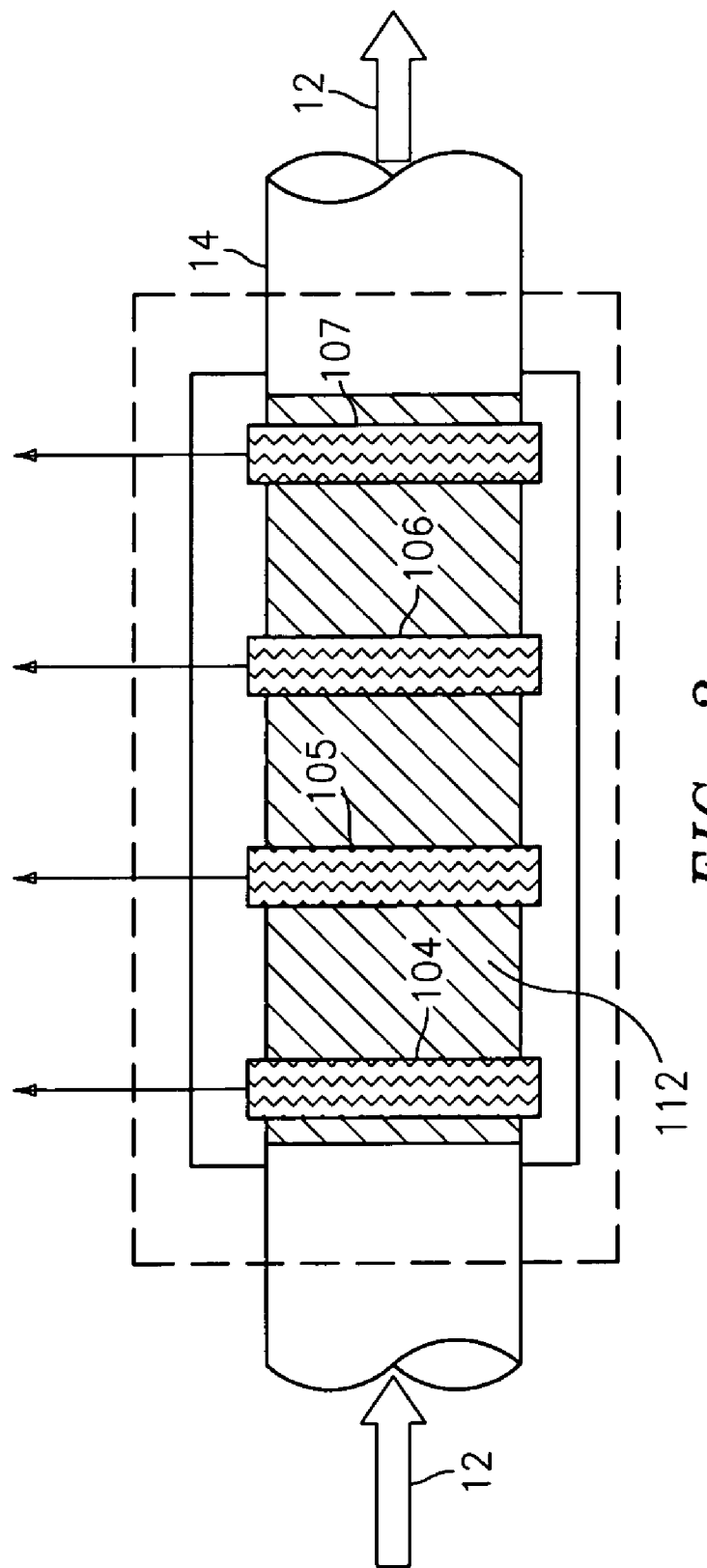
FIG. 3 is a side elevational view of a plurality of pressure sensors, having PVDF, clamped to the outer surface of the pipe, in accordance with the present invention.

Furthermore the present invention contemplates that each of the pressure sensors 15–18 may include a piezoelectric sensor 104–107 that provides a piezoelectric material to measure the unsteady pressures of the fluid 12 as shown in FIG. 3. The piezoelectric material, such as the polymer, polarized fluoropolymer, polyvinylidene fluoride (PVDF), measures the strain induced within the process pipe 14 due to unsteady pressure variations within the fluid 12. Strain within the pipe 14 is transduced to an output voltage or current by the attached piezoelectric sensors 104–107.

The PVDF material forming each piezoelectric sensor 104–107 may be adhered to the outer surface of a steel strap 112 that extends around and clamps onto the outer surface of the pipe 14. The piezoelectric sensing element is typically conformal to allow complete or nearly complete circumferential measurement of induced strain. The sensors 104–107 can be formed from PVDF films, co-polymer films, or flexible PZT sensors, similar to that described in "Piezo Film Sensors technical Manual" provided by Measurement Specialties, Inc. of Fairfield, N.J., which is incorporated herein by reference. The advantages of this technique are the following:

1. Non-intrusive flow rate measurements
2. Low cost
3. Measurement technique requires no excitation source. Ambient flow noise is used as a source.
4. Flexible piezoelectric sensors can be mounted in a variety of configurations to enhance signal detection schemes. These configurations include a) co-located sensors, b) segmented sensors with opposing polarity configurations, c) wide sensors to enhance acoustic signal detection and minimize vertical noise detection, d) tailored sensor geometries to minimize sensitivity to pipe modes, e) differencing of sensors to eliminate acoustic noise from vertical signals.
5. Higher Temperatures (140C) (co-polymers)

EXAMPLES

Figure 4:
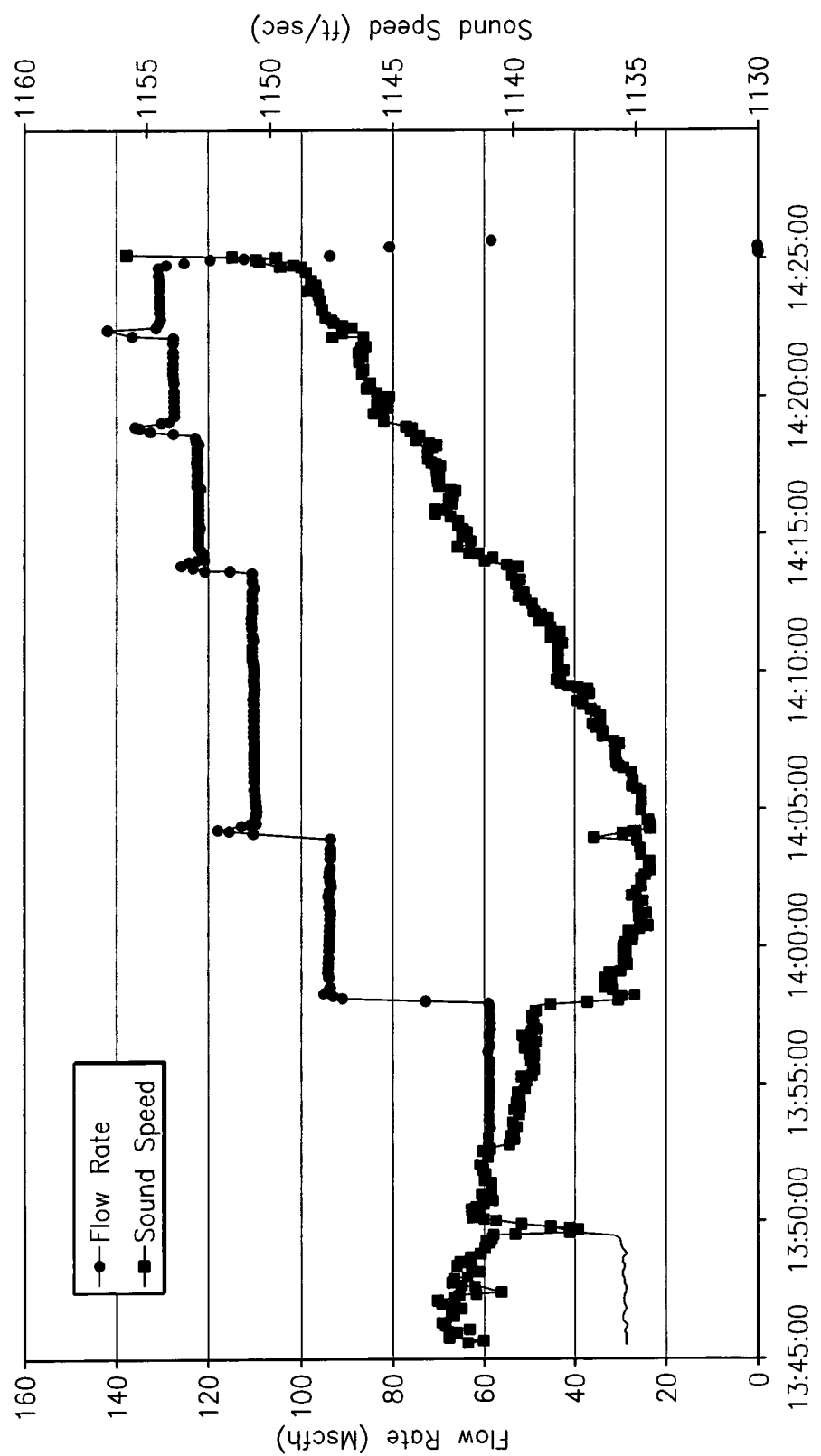
FIG. 4 is plot of data showing the measured speed of sound and the volumetric flow rate outputs from an apparatus embodying the present invention.

The method of flow measurement described herein was demonstrated on a 6-inch schedule 40 steel pipe flowing air at near atmospheric pressure. The Mach number range was 0.07 to 0.16. A six-sensor PVDF mono-band was used to measure the acoustic field in the pipe, similar to that described in U.S. Provisional Patent Application, Ser. No. 60/451,685 filed Mar. 4, 2003, which in incorporated herein by reference. A reference measurement was made with an orifice plate that had a relatively high uncertainty estimated at 5–10%. The results of one series of tests are shown in FIG. 4.

A typical k-ω plot of the data is as shown in FIG. 2. Note that the slope of the acoustic ridge 61 with positive wavenumber is greater than the slope of the acoustic ridge 62 with negative wavenumber indicating that the apparent speed in the direction of the flow is faster than in the direction opposite of the flow. Specifically, the slope of the acoustic ridge 61, which is indicative of the speed of sound in the direction of the flow, is 1305 ft/sec, while the slope of the acoustic ridge 62, which is indicative of the speed of sound against the direction of the flow, is 941 ft/sec. Therefore, the speed of sound of the acoustic wave propagating through the fluid (if the liquid was not flowing) is 1123 ft/sec. The velocity of the flow ($V_{mix}$) is therefore 182 ft/s ([1305 ft/sec–941 ft/sec]/2).

Figure 5:
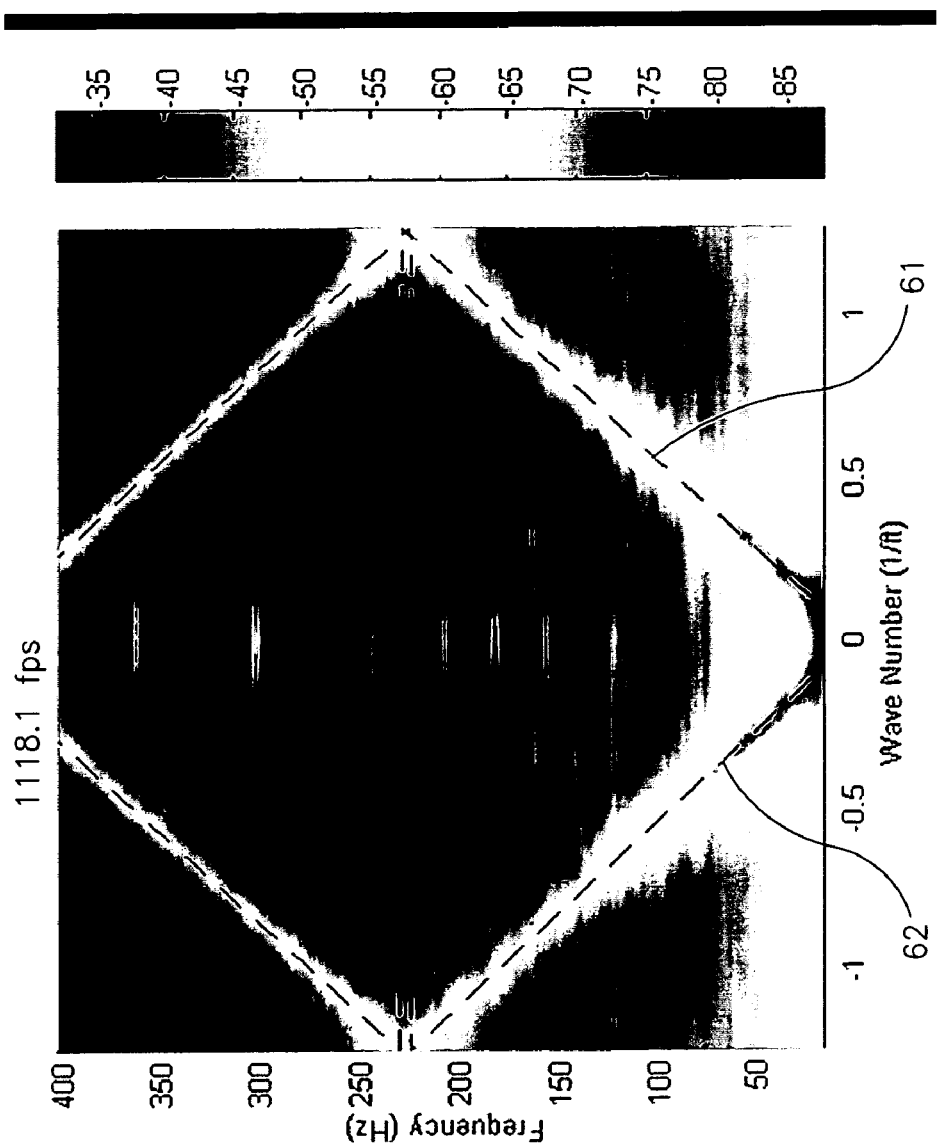
FIG. 5 is a kω plot of data processed from an array of pressure sensors use to measure the speed of sound propagating through a saturated vapor/liquid mixture flowing in a pipe, in accordance with the present invention.

Further, FIG. 5 illustrates the ability of the present invention to determine the velocity of a fluid moving in a pipe. FIG. 5 comprises plots of data from an actual test run of a flow meter in accordance with the invention as described herein above. FIG. 5 shows a wavenumber-frequency plot (k-w plot) of unsteady pressure data collected with a flow-meter comprising a 4-sensor axial array in an atmospheric pressure loop flowing air at a velocity of approximately 40 ft/sec. The contours represent the relative signal power at all combinations of frequency and wavenumber. The highest power "ridges" represent the acoustic wave with slope of the ridges 61 and 62 being equal to the propagation speed. Note that the acoustic ridges 61 and 62 "wrap" to the opposite side of the plot at the spatial Nyquist wavenumber equal to ±3.14 in this case (i.e. the acoustic ridge that slopes up and to the right starting at the bottom of the plot, the right-side ridge 61, wraps to the left side of the plot at approximately 550 Hz and continues sloping up and to the left). As previously noted, he right-side ridge 61 represents the acoustic wave traveling in the same direction as the bulk flow and therefore its slope is steeper than the left-side ridge 62 that represents the acoustic wave traveling in the opposite direction of the bulk flow. This indicates that the acoustic wave traveling in the same direction of the flow is traveling faster than the acoustic wave traveling in the opposite direction of the bulk flow relative to the stationary sensors 15–18 located on the pipe 14.

The present invention provides an apparatus and method to measure velocity and volumetric flow rate of single phase and/or multiphase fluids having non-negligible axial Mach numbers used, emitted and/or processed in an industrial fluid flow process, such as, for example, in chemical, pharmaceutical, paper/pulp, petroleum and power generation industries. The knowledge or determination of the velocity and volumetric flow rate of a fluid system may be used to provide feedback of the flow process to improve quality control of the flow process or to detect problems or needed maintenance.

While the present invention is capable of measuring liquid droplets suspended in a vapor, one will appreciate that other multi-phase mixtures or flows may be measured using an array of sensors, such as solid particles suspended in a fluid. It is further recognized the effects of dispersion on large droplets of liquid would be similar to large solid particles dispersed in a fluid (e.g., gas or air), and thus similar considerations when measuring the air-to-particle ratio and particle size should be addressed.

It should be understood that any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein and thereto without departing from the spirit and scope of the present invention.

What is claimed is:

1. An apparatus for measuring at least one parameter of a fluid having a non-negligible axial Mach number passing through a pipe, the apparatus comprising:
    a spatial array of at least two pressure sensors disposed at different axial locations along the pipe, and each measuring an unsteady pressure within the pipe at a corresponding axial location, each of the pressure sensors providing a pressure signal in response to a first one-dimensional acoustic wave propagating in a first axial direction and a second one-dimensional acoustic wave propagating in a second axial direction within the pipe, the first axial direction being opposite the second axial direction; and
    a signal processor, responsive to the pressure signals, which provides a first acoustic signal indicative of a speed of the first acoustic wave and a second acoustic signal indicative of a speed of the second acoustic wave.

2. The apparatus of claim 1 wherein the signal processor, responsive to the first acoustic signal and the second acoustic signal, provides a velocity signal indicative of a velocity of the fluid passing through the pipe.

3. The apparatus of claim 2 wherein the signal processor, responsive to the velocity signal, provides a rate signal indicative of a flow rate of the fluid passing through the pipe.

4. The apparatus of claim 2 wherein the signal processor determines the velocity of the fluid using a difference between the speed of the first acoustic wave and the speed of the second acoustic wave.

5. The apparatus of claim 1 wherein the signal processor comprises logic that calculates a speed at which sound propagates through the fluid passing through the pipe.

6. The apparatus of claim 5 wherein the signal processor determines the speed at which sound propagates through the fluid using a ratio of the speed of the first acoustic wave and the speed of the second acoustic wave.

7. The apparatus of claim 1 wherein the signal processor comprises logic that calculates a frequency based signal for each of the pressure signals.

8. The apparatus of claim 1 wherein at least one of the pressure sensors measures strain on the pipe.

9. The apparatus of claim 1, further comprising:
    at least one acoustic source for injecting the first and second one-dimensional acoustic waves into the fluid.

10. A method for measuring at least one parameter of a fluid having a non-negligible axial Mach number passing through a pipe, the method comprising:
    measuring unsteady pressures within the pipe at at least two predetermined axial measurement locations along the pipe to provide a pressure signal in response to a first one-dimensional acoustic wave propagating in a first axial direction and a second one-dimensional acoustic wave propagating in a second axial direction within the pipe, the first axial direction being opposite the second axial direction;
    determining a first acoustic signal indicative of the speed of the first acoustic wave; and
    determining a second acoustic signal indicative of the speed of the second acoustic wave.

11. The method of claim 10 further including:
    determining a velocity signal indicative of a velocity of the fluid passing through the pipe in response to the first acoustic signal and the second acoustic signal.

12. The method of claim 11 further including:
    determining a rate signal indicative of a flow rate of the fluid passing through the pipe in response to the first acoustic signal and the second acoustic signal.

13. The method of claim 11, wherein the signal processor determines the velocity of the fluid using a difference between the speed of the first acoustic wave and the speed of the second acoustic wave.

14. The method of claim 10, further comprising:
    calculating a speed at which sound propagates through the fluid using a ratio of the speed of the first acoustic wave and the speed of the second acoustic wave.

15. The method of claim 10 wherein determining the first and second acoustic signals includes determining a frequency based signal for each of the pressure signals.

16. The method of claim 10 wherein measuring unsteady pressures includes measuring strain on the pipe.

17. The method of claim 10, further comprising:
injecting the first and second one-dimensional acoustic waves into the fluid.

18. An apparatus for measuring at least one parameter of a fluid having a non-negligible axial Mach number passing through a pipe, the apparatus comprising:
a spatial array of at least two pressure sensors, disposed at different axial locations along the pipe, and each measuring an unsteady pressure within the pipe at a corresponding axial location, each of the pressure sensors providing a pressure signal in response to a first one-dimensional acoustic wave propagating in a first axial direction and a second one-dimensional acoustic wave propagating in a second axial direction within the pipe, the first axial direction being opposite the second axial direction; and
a signal processor, responsive to the pressure signals, which provides a velocity signal in response to a difference between a speed of the first acoustic wave and a speed of the second acoustic wave.

19. The apparatus of claim 18 wherein the signal processor, responsive to the velocity signal, provides a rate signal indicative of a flow rate of the fluid passing through the pipe.

20. The apparatus of claim 18 wherein the signal processor determines a speed at which sound propagates through the fluid using a ratio of the speed of the first acoustic wave and the speed of the second acoustic wave.

21. A method for measuring the volumetric flow rate of a fluid having a non-negligible axial Mach number passing through a pipe, the method comprising:
measuring unsteady pressures within the pipe at at least two predetermined axial measurement locations along the pipe to provide a pressure signal in response to a first one-dimensional acoustic wave propagating in a first axial direction and a second one-dimensional acoustic wave propagating in a second axial direction within the pipe, the first axial direction being opposite the second axial direction; and
determining a velocity of the fluid in response to a difference between a speed of the first acoustic wave and a speed of the second acoustic wave.

22. The method of claim 21 further comprising:
determining a flow rate of the fluid in response to the velocity of the fluid.

23. The method of claim 21, further comprising:
determining a speed at which sound propagates through the fluid using a ratio of the speed of the first acoustic wave and the speed of the second acoustic wave.

24. An apparatus for measuring at least one parameter of a fluid having a non-negligible axial Mach number passing through a pipe, the apparatus comprising:
a means for providing a pressure signal in response to a first one-dimensional acoustic wave propagating in a first axial direction and a second one-dimensional acoustic wave propagating in a second axial direction within the pipe, the first axial direction being opposite the second axial direction; and
a means for providing a velocity signal in response to a difference between a speed of the first acoustic wave and a speed of the second acoustic wave.

25. The apparatus of claim 24 wherein the means for providing the velocity signal further provides a rate signal indicative of a flow rate of the fluid passing through the pipe.

26. The apparatus of claim 1, wherein the spatial array includes 3, 4, 5, 6, 7, 8, 9, 10, 11, 12, 13, 14, 15, 16, 17, 18, 19 or 20 pressure sensors.

27. The apparatus of claim 1, wherein the at least two pressure sensors are attached to the outer surface of the pipe.

28. The apparatus of claim 1, wherein the signal processor determines the speed of the first and/or second acoustic wave in response to an array processing algorithm.

29. The apparatus of claim 1, wherein the signal processor determines the slope of an acoustic ridge in the k-ω plane to determine the speed of the first and/or second acoustic wave.

30. The method of claim 10, wherein the measuring of unsteady pressures within the pipe is 3, 4, 5, 6, 7, 8, 9, 10, 11, 12, 13, 14, 15, 16, 17, 18, 19 or 20 axial measurement locations along the pipe.

31. The method of claim 10, wherein the determining of the speed of the first and/or second acoustic wave is in response to an array processing algorithm.

32. The method of claim 10, wherein the determining of the speed of the first and/or second acoustic wave is provided by determining the slope of an acoustic ridge in a k-ω plane.

33. The apparatus of claim 18, wherein the spatial array includes 3, 4, 5, 6, 7, 8, 9, 10, 11, 12, 13, 14, 15, 16, 17, 18, 19 or 20 pressure sensors.

34. The apparatus of claim 18, wherein the at least two pressure sensors are attached to the outer surface of the pipe.

35. The apparatus of claim 18, wherein at least one of the pressure sensors measures strain on the pipe.

36. The apparatus of claim 18, further comprising at least one acoustic source for injecting the first and second one-dimensional acoustic waves into the fluid.

37. The apparatus of claim 18, wherein the signal processor determines the speed of the first and/or second acoustic wave in response to an array processing algorithm.

38. The apparatus of claim 18, wherein the signal processor determines the slope of an acoustic ridge in the k-ω plane to determine the speed of the first and/or second acoustic wave.

39. The method of claim 21, wherein the measuring of unsteady pressures within the pipe are at 3, 4, 5, 6, 7, 8, 9, 10, 11, 12, 13, 14, 15, 16, 17, 18, 19 or 20 axial measurement locations along the pipe.

40. The method of claim 21, further comprises injecting the first and second one-dimensional acoustic waves into the fluid.

41. The method of claim 21, wherein further comprises determining the speed of the first and/or second acoustic wave in response to an array processing algorithm.

42. The method of claim 21, wherein further comprises determining the slope of an acoustic ridge in the k-ω plane to determine the speed of the first and/or second acoustic wave.

43. The apparatus of claim 24, further comprises means for injecting the first and second one-dimensional acoustic waves into the fluid.

44. The apparatus of claim 24, further comprises means for determining the speed of the first and/or second acoustic wave in response to an array processing algorithm.

45. The apparatus of claim 24, further comprises means for determining the slope of an acoustic ridge in the k-ω plane to determine the speed of the first and/or second acoustic wave.

* * * * *